(12) United States Patent
Rousseau et al.

(10) Patent No.: US 8,088,083 B2
(45) Date of Patent: Jan. 3, 2012

(54) SYSTEM FOR MEASUREMENT OF HEAD POSITION AND MEASUREMENT TOOL FOR SUCH A SYSTEM

(75) Inventors: Thomas Rousseau, Stockholm (SE); Per Carlsson, Taby (SE); Magnus Lindfors, Stockholm (SE)

(73) Assignee: Elekta AB (Publ), Stockholm (SE)

( * ) Notice: Subject to any disclaimer, the term of this patent is extended or adjusted under 35 U.S.C. 154(b) by 288 days.

(21) Appl. No.: 12/428,028

(22) Filed: Apr. 22, 2009

(65) Prior Publication Data

US 2009/0270769 A1 Oct. 29, 2009

(30) Foreign Application Priority Data

Apr. 23, 2008 (EP) .................................... 08155023

(51) Int. Cl.
*A61B 5/103* (2006.01)
*A61B 5/117* (2006.01)

(52) U.S. Cl. ........................................ 600/595; 600/587
(58) Field of Classification Search .................. 600/587, 600/595, 372, 382, 383, 384, 407, 410, 414, 600/415, 417, 544, 545, 561
See application file for complete search history.

(56) References Cited

U.S. PATENT DOCUMENTS

| 2,400,371 | A | 5/1946 | Reeser |
| 5,072,174 | A | 12/1991 | Weber |
| 2006/0233303 | A1* | 10/2006 | Carlsson et al. ................ 378/68 |

FOREIGN PATENT DOCUMENTS

| WO | WO-2006/108634 A1 | 10/2006 |
| WO | WO-2006/118509 A1 | 11/2006 |
| WO | WO-2007/040507 A2 | 4/2007 |

* cited by examiner

*Primary Examiner* — Jeffrey G Hoekstra
(74) *Attorney, Agent, or Firm* — Birch, Stewart, Kolasch & Birch, LLP

(57) ABSTRACT

The present invention relates to the field of radiation therapy. In particular, the relates to a system for measuring the position of a head of a patient during neurological diagnosis, therapy or surgery, in particular during radiation therapy relatively a frame adapted to be fixated to a radiation therapy unit. The invention also relates to a head cap and a measurement tool for use in such a system, and to a method measuring the position of a head of a patient by means of a system mentioned above during neurological diagnosis, therapy or surgery, in particular during radiation therapy relatively a frame adapted to be fixated to a radiation therapy unit. The measurement tool is adapted to measure a distance between the head and the head cap via a through hole by means of an elongated element having an end being adapted to abut against the head during a measurement, wherein the measurement tool is adapted to obtain at least one measurement value indicating a position of the head in relation to the head cap substantially without operator interaction.

14 Claims, 5 Drawing Sheets

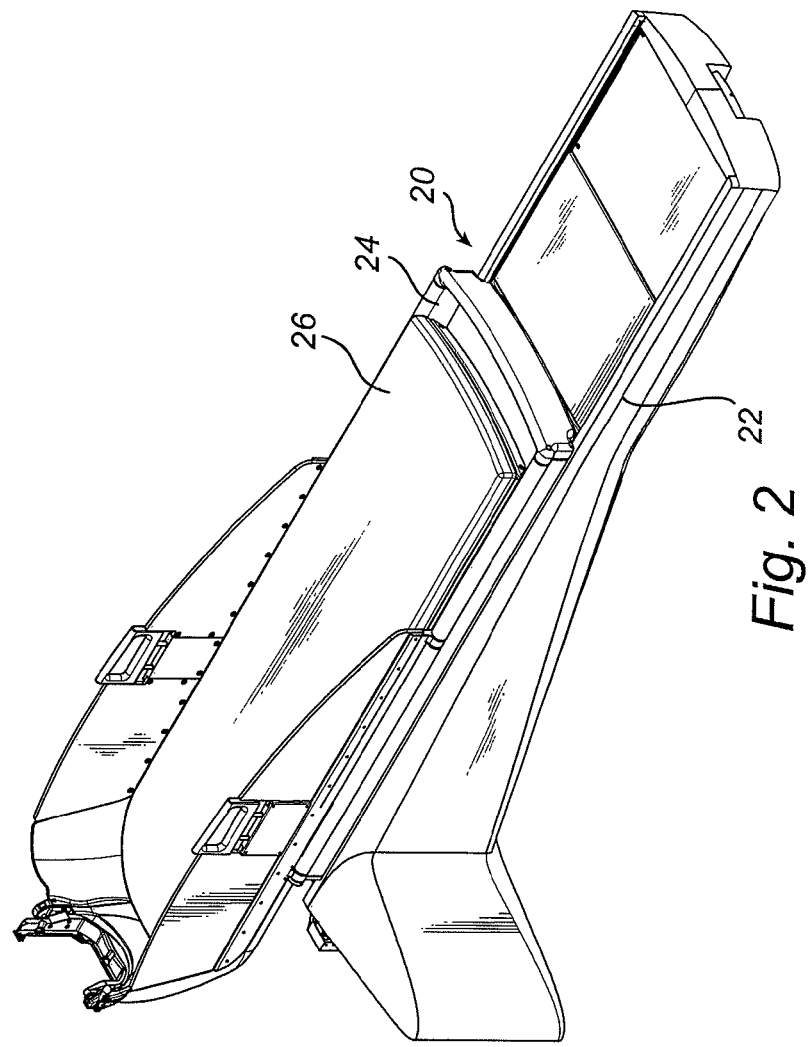
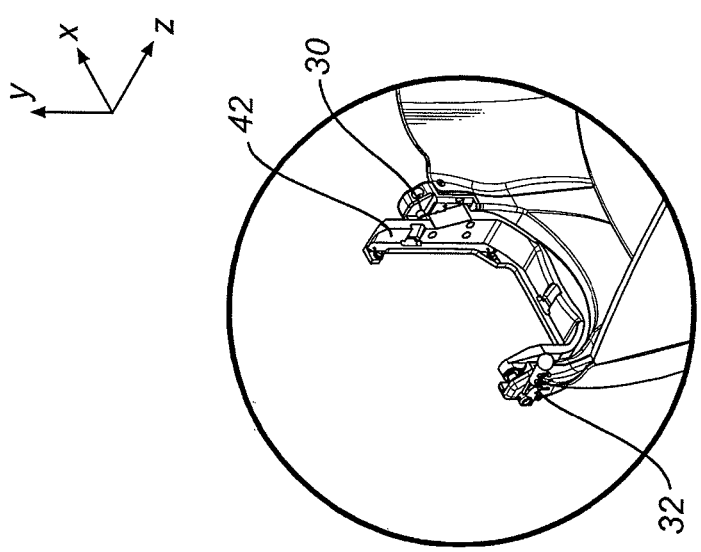
Fig. 2
Fig. 3

SYSTEM FOR MEASUREMENT OF HEAD POSITION AND MEASUREMENT TOOL FOR SUCH A SYSTEM

FIELD OF THE INVENTION

The present invention relates to the field of radiation therapy. In particular, the relates to a system for measuring the position of a head of a patient during neurological diagnosis, therapy or surgery, in particular during radiation therapy relatively a frame adapted to be fixated to a radiation therapy unit.

The invention also relates to a head cap and a measurement tool for use in such a system, and to a method measuring the position of a head of a patient by means of a system mentioned above during neurological diagnosis, therapy or surgery, in particular during radiation therapy relatively a frame adapted to be fixated to a radiation therapy unit.

BACKGROUND OF THE INVENTION

The development of surgical techniques have made great progress over the years. For instance, for patients requiring brain surgery, non-invasive surgery is now available which is afflicted with very little trauma to the patient.

Stereotactic radiosurgery is such a minimally invasive treatment modality that allows delivery of a large single dose of radiation to a specific intracranial target while sparing surrounding tissue. Unlike conventional fractionated radiotherapy, stereotactic radiosurgery does not rely on, or exploit, the higher radiosensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radioresistant lesions can be treated. Because destructive doses are used, however, any normal structure included in the target volume is subject to damage.

One such non-invasive radiotherapy technique is so called LINAC (Linear Accelerator) radio therapy. In a LINAC radiotherapy system, a collimated x-ray beam is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain.

Another system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is, for example, referred to and described in U.S. Pat. No. 4,780,898.

In the system, the head of a patient is immobilized in a stereotactic instrument which defines the location of the treatment volume in the head. Further, the patient is secured in a patient positioning system which moves the entire patient so as to position the treatment volume in coincidence with the focus point of the radiation unit of the system.

Consequently, in radiotherapy systems, such as a LINAC system or a Leksell Gamma Knife® system, it is of a high importance that the positioning system which moves the patient so as to position the treatment volume in coincidence with the focus point of the radiation unit of the system is accurate and reliable. That is, the positioning system must be capable of position the treatment volume in coincidence with the focus point at a very high precision. This high precision must also be maintained over time.

Hence, in order to obtain as favorable clinical effect as possible during the therapy is it of an utmost importance that the radiation reaches and hits the target, i.e. the treatment volume, with a high precision and thereby spares the healthy tissue being adjacent to and/or surrounding the treatment volume. To achieve this, the patient must be immobilized during a therapy session and, moreover, the position of the head of the patient must be the same in a therapy session as in a reference position, i.e. the position during the session when the pictures to create the therapy plan were captured by means of, for example, Computerized Tomography Imaging (CT-imaging). In fractionated radiotherapy where the patient is docked in and out of the radiation therapy system at each therapy session, it must thus be secured that the patient is positioned in exact the same way as in the session when the pictures were captured to create the therapy plan.

One prior art method for enabling measurements of the head of a patient and for fixating the head of the patient during neurological diagnosis, therapy or surgery, in particular during radiation therapy relatively a frame adapted to be fixated to a radiation therapy unit is a stereotactic frame provided with pin support members in form of posts having fixation pins for invasive fixation to the skull of a patient. In use during for example MRI (Magnetic Resonance Imaging) diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a MRI table. This kind of frame is obviously not suitable for so called fractionated therapy.

Thus, there is a need within the art of improved means that enables accurate and fast measurements of a position of a head of a patient relative a radio therapy unit to secure that the patient is positioned in exact alignment to a reference position or at a known position in relation to the reference position.

SUMMARY OF THE INVENTION

An object of the present invention is to provide improved means for repeatable and accurate measurements of a position of a head of a patient relative a radio therapy unit to secure that the patient is positioned in exact alignment to a reference position or at a known position in relation to the reference position.

A further object of the present invention is to provide improved means for obtaining input data regarding the shape and size of the head for the dosage planning in connection with radiation therapy.

Still another object of the present invention is to provide means for accurate and fast measurements of a position of a head of a patient relative a reference position.

Yet another object of the present invention is to provide means for securing that the patient can be docked to the radio therapy unit in a repeatable way to guarantee that the patient is positioned in exact alignment to a reference position or at a known position in relation to the reference position during fractionated therapy.

These and other objects are achieved by providing a system, a measurement tool, a head cap, and a method having the features defined in the independent claims. Preferred embodiments are defined in the dependent claims.

According to a first aspect of the present invention, there is provided a method for measuring a position of a head of a patient during neurological diagnosis, therapy or surgery, relative to a frame adapted to be fixated to diagnosis equipment such as a Computer Tomograph or a radiation therapy unit, the frame being fixated relative to the patient, the method comprising the steps:

providing a head cap adapted to be mounted at the frame such that the head cap is fixed relatively the frame, the head cap being rigid and shaped to at least partly surround the head of the patient during neurological diagnosis, wherein the head cap comprises a number through holes;

fixating the frame on the head of the patient;

fixating the head cap to the frame thereby surrounding the head:

providing a measurement tool adapted to measure a distance between the head and the head cap via a through hole by means of an elongated element having an end being adapted to abut against the head during a measurement, wherein the measurement tool is adapted to obtain at least one measurement value indicating a position of the head in relation to the head cap substantially without operator interaction; and performing a measurement session in order to obtain a plurality of measurement values each including a distance between the head of the patient and a respective reference point of the head cap using the measurement tool.

The measurement tool is adapted to obtain at least one digital measurement value when placed in abutment against the head of the patient. When placed against the head, the measurement tool obtains or provides the measurement value automatically and substantially without operator or user interaction where an operator needs to manually read the measurement values. Thereby, it is possible to obtain very accurate measurement values and the process for obtaining measurement values is efficient and simple for the operator or user. The impact from the operator at the measurement can thereby be minimized which also contributes to the improvement in accuracy and reliability, and, in addition, the handling of the measurement tool is facilitated and the ease of use is improved. The measurement tool adapted to deliver digital measurement values without operator interaction when placed in abutment against the head of the patient in cooperation with a head cap surrounding the head of the patient comprising a number of defined measurement locations, where the head cap is arranged for cooperation with the measurement tool.

According to a second aspect of the present invention, there is provided a system for measuring a position of a head of a patient during neurological diagnosis, therapy or surgery, relative to a frame adapted to be fixated to diagnosis equipment such as a Computer Tomograph or a radiation therapy unit, the frame being fixated relative to the patient. The system comprises a head cap adapted to be mounted at the frame such that the head cap is fixed relatively the frame, the head cap being rigid and shaped such that is at least partly can surround the head of the patient when placed on the head, wherein the head cap comprises a number through holes, and a measurement tool adapted to measure a distance between the head and the head cap via a through hole by means of an elongated element having an end being adapted to abut against the head during a measurement to obtain at least one measurement value, wherein the measurement tool is adapted to obtain at least one measurement value indicating a position of the head in relation to the head cap substantially without operator interaction.

According to a third aspect of the present invention, there is provided a head cap for use in a system according to the second aspect of the present invention for measuring a position of a head of a patient during neurological diagnosis, therapy or surgery, relative to a frame fixated to diagnosis equipment such as a Computer Tomograph or a radiation therapy unit, the frame being adapted to be fixated relative to the patient, wherein the head cap is adapted to be mounted at the frame such that the head cap is fixed relatively the frame, the head cap being rigid and shaped such that the head of the patient is at least partly surrounded when the head cap is placed on the head, wherein the head cap comprises a number of through holes, and wherein the head cap is arranged to cooperate with a measurement tool according to the fourth aspect According to a further aspect of the present invention, there is provided a measurement tool for use in a system according to the second aspect of the present invention for measuring a position of a head of a patient during neurological diagnosis, therapy or surgery, relative to a frame adapted to be fixated to diagnosis equipment such as a Computer Tomograph or a radiation therapy unit, the frame being fixated relative to the patient, the system further comprising a head cap adapted to be mounted at the frame such that the head cap is fixed relatively the frame, the head cap being rigid and shaped such that the head of the patient is at least partly surrounded when the head cap is placed on the head, and wherein the head cap comprises a number of through holes, wherein the measurement tool is adapted to measure a distance between the head and the head cap via a through hole by means of an elongated element having an end being adapted to abut against the head during a measurement, wherein the measurement tool is adapted to obtain at least one measurement value indicating a position of the head in relation to the head cap without operator interaction.

Thus, the present invention is based on the idea of using a measurement tool adapted to deliver digital measurement values without operator interaction when placed in abutment against the head of the patient. Thereby, it is possible to obtain very accurate measurement values and the process for obtaining measurement values is efficient and simple for the operator or user. The impact from the operator is also minimized which also contributes to the improvement in accuracy and reliability, and, in addition, the handling of the measurement tool is facilitated and the ease of use is improved. The measurement tool is used in cooperation with a rigid head cap surrounding the head of the patient comprising a number of defined measurement locations arranged in substantially plane structures each including at least one measurement location or through hole enabling accurate and repeatable measurements of a distance between head cap, e.g. the inner surface of the head cap, and the skull bone of the patient. The head cap is arranged to be placed flush against the frame thereby ensuring that the patient can be docked to the radio therapy unit in a repeatable way to guarantee that the patient is positioned in exact alignment to a reference position, both during reference measurements and during a head position measurement at a treatment session. The term "substantially without operator interaction" should be interpreted as that the measurement tool is capable of performing the actual measurement without interaction from the operator. However, the process of obtaining a measurement value can be initiated by the operator by, for example, pressing a button of the measurement tool. Furthermore, a measurement value can be transferred automatically or as a result of receiving an instruction from the operator from the measurement tool to a, for example, a monitoring device. However, this transfer of measurement values can also be initiated by the operator, for example, by pressing a button, but the actual transferring process will be automatic.

The present invention may be used to determine a reference position of the head before the therapy is initiated and to determine the position of the head during the fractionated therapy, i.e. to secure that the patient is docked into and out of the radio therapy system in a repeatable manner.

Furthermore, due to the fact that the measurements can be performed plane by plane rotations and rotational errors can be captured, which entail that the accuracy and repeatability of the measurements can be further increased. A rotation in such that it would affect the treatment performance would in most cases yield a position deviation in any of the substantially plane measurements. In other words, by not measuring in the radial direction directed towards the centre of the head, but to use a head cap more rectangular shaped and to measure perpendicular to the surfaces of the cap, the rotational errors are captured as translational errors in any of the measurements.

According to embodiments of the present invention, the head cap comprises substantially plane structures each including at least one through hole, i.e. the head cap is essentially shaped as a cube. Thereby, it is possible to obtain a number of measurement values in the X-plane, Y-plane, and Z-plane, respectively, and by calculating an average value for the X-values, Y-values, and Z-values, respectively, an estimate for an error in the X direction, Y direction, and Z direction, respectively, can be determined. In one embodiment of the present invention, the measurement tool comprises an analyzing unit adapted to determine whether at least one predetermined condition is satisfied. The measurement tool is adapted to obtain the at least one measurement value indicating a position of the head in relation to the head cap when the at least one predetermined condition is satisfied. For example, the at least one predetermined condition is that a time delay having a predetermined length has elapsed. Further, the at least one predetermined conditions is that measurement conditions are found to be stable. Thereby, the accuracy and reliability of the measurements can be improved even further since it can be verified that the measurement conditions are stable and as comparable to the conditions at earlier measurement sessions as possible. Moreover, the impact from the operator is also minimized which also contributes to the improvement in accuracy and reliability, and, in addition, the handling of the measurement tool is facilitated and the ease of use is improved.

In another embodiment of the present invention, the analyzing unit is adapted to determine a distance change over time, wherein a distance change over time being lower than a predetermined level is an indication of that the measurement conditions are stable. This is because when a certain pressure is applied to the skin of a human, there is a slight delay before the skin and flesh has "come to rest" under the pressure so that the distance over time is stable enough. This also contributes to the improvement of the accuracy and reliability of the measurements since it can be verified that the measurement conditions are stable and as comparable to the conditions at earlier measurement sessions as possible.

Furthermore, the measurement tool may comprise a pressure indicator adapted to indicate an applied pressure of the measurement tool against the head during a measurement, wherein the measurement conditions are found to be stable when a predetermined pressure is indicated. This further contributes to the improvement of the accuracy and reliability of the measurements since it can be verified that the measurement conditions are stable and as comparable to the conditions at earlier measurement sessions as possible.

In another embodiment of the present invention, the measurement tool is adapted to communicate with a monitoring device adapted to receive the at least one measurement value from the measurement tool. The monitoring device may for example be a personal computer or a lap top computer and the transfer of, for example, measurement values can be made wirelessly or via a physical communication link. Thus, measurement data from the measurement tool can be exported to the monitoring device where is can be displayed on a display unit and/or stored a memory unit.

According to an embodiment of the present invention, the head cap comprises a first structure including at least one through hole arranged such that an imaginary line passing through the hole is substantially parallel with a first axis of a three dimensional orthogonal reference coordinate system of the frame, wherein the head cap comprises a second structure including at least one through hole arranged such that an imaginary line passing through the hole is substantially parallel with a second axis of the reference coordinate system, and wherein the head cap comprises a third structure including at least one through hole arranged such that an imaginary line passing through the hole is substantially parallel with a third axis of the reference coordinate system. Thereby, it is possible to perform several measurements of a distance between head cap, e.g. the inner surface of the head cap, and the skull bone of the patient for three perpendicular axes and thus the accuracy and repeatability of the measurements can be increased.

In one embodiment of the present invention, a number of measurements are performed to obtain a number of measurements values for each axis and one measurement result per axis is created by means of, for example, averaging the obtained measurement values.

In one embodiment of the present invention, each through hole is shaped as a substantially circular guide channel. Thereby, the measurement tool can be guided to an exact measurement position and the measurement tool is also stabilized during the measurement. This will lead to increased accuracy and repeatability of the measurements.

According to an embodiment of the present invention, the elongated element of the measurement tool comprises a rod being adapted to pass through the through holes, wherein the rod having an end being adapted to abut against the head is adapted to be placed against the head via a through hole during a measurement.

In a further embodiment of the present invention, a distance measurement tool adapted to deliver a measure indicating a distance between the head and a reference point of the head cap, wherein each through hole has a reference point.

Alternatively, the head cap is rigid and shaped to at least mainly surround the head of the patient.

According to an embodiment of the present invention, the elongated element of the measurement tool is spring-loaded.

In a further embodiment of the present invention, the measurement tool comprises a pressure indicator adapted to indicate an applied pressure of the measurement tool against the head during a measurement, wherein each measurement can be performed at a predetermined pressure. Thereby, it is possible to further increase the accuracy and repeatability of the measurements due to the fact that measurement insecurity caused by irregularities in, for example, skin thickness and hair distribution can be reduced or minimized.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

Preferred embodiments of the invention will now be described in greater detail with reference to the accompanying drawings, in which

FIG. 2 illustrates the positioning system used in the system of FIG. 1;

FIG. 3 illustrates a part of the positioning system including the engagement points for holding a fixation frame in more detail;

DESCRIPTION OF PREFERRED EMBODIMENTS

Figure 1:
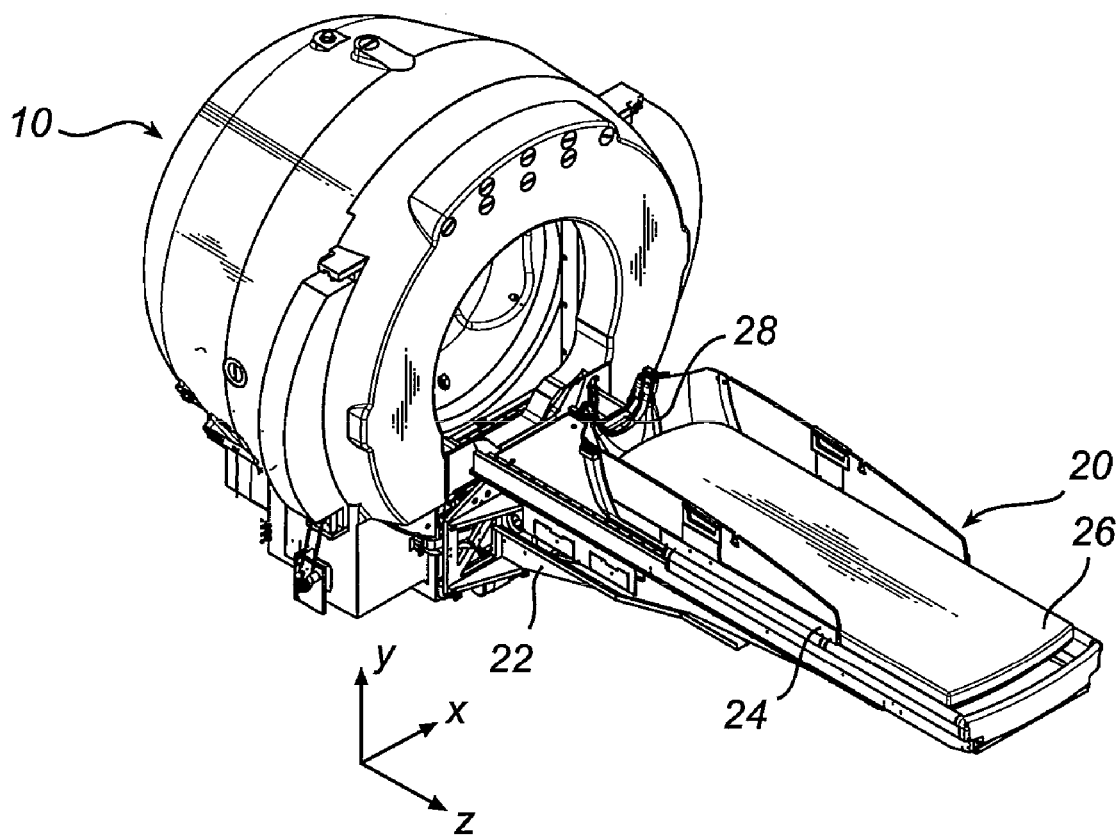
FIG. 1 illustrates the general principle of a radiation therapy system in which the present invention may be used.

First, with reference to FIGS. 1-3, a radiation therapy system for which the present invention is applicable comprises a radiation unit 10 and a patient positioning unit 20 will be described. In the radiation unit 10, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels. Examples of collimator arrangements in radiation therapy systems applicable to the present invention can be found in U.S. Pat. No. 6,931,096, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the present inventions is also applicable to LINAC radiosurgical systems, in which a collimated x-ray beam is focused on a stereotactically identified intracranial target and the gantry of the LINAC rotates around the patient, producing an arc of radiation focused on the target.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or frame, either directly or via an adapter unit 42, see FIG. 3. A head can according to the present invention, for example, a rigid casing enclosing the head of the patient (which will be described in more detail below with reference to FIGS. 4 and 5) is attachable to the patient fixation frame, see FIG. 3.

The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system. A measurement tool according to the present invention (which will be described in more detail below with reference to FIG. 5) may thus use the same coordinate system, i.e. the fixation unit coordinate system.

The fixation arrangement 28 comprises two engagement points 30, 32, which are arranged for preventing the patient fixation unit from translational and/or rotational movement in relation to the movable carriage 24.

As can be understood from FIGS. 1 and 2, the described embodiment concerns a radiation therapy system for providing gamma radiation therapy to a target volume in the head of human patient. Such therapy is often referred to as stereotactic radio surgery. During therapy, the patient head is fixed in a fixation unit in the form of a stereotactic head frame, which comprises engagement points adapted for engagement with the engagement points 30, 32 of the radiation therapy system. Thus, during the stereotactic radio surgery, the head of the patient is fixed in the stereotactic frame, which in turn is fixedly attached to the patient positioning system via the engagement points 30, 32. During movement of the treatment volume in the head of the patient in relation to the radiation focus point, along the three orthogonal axes x, y, and z shown in FIG. 1, the entire patient is moved along the axes. Thus, there is no relative movement between the head frame and the carriage 24 of the patient positioning system 20.

Figure 4:
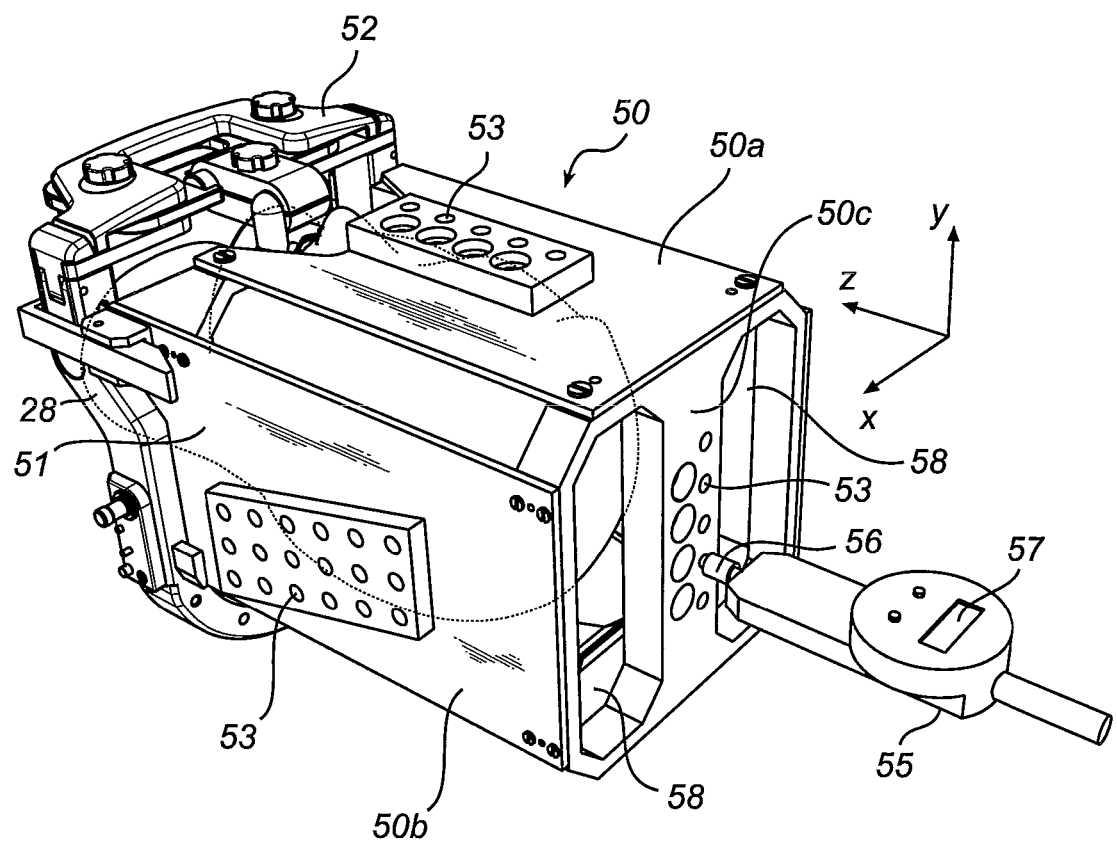
FIG. 4 illustrates the head cap and measurement tool according to an embodiment of the present invention.
Figure 5:
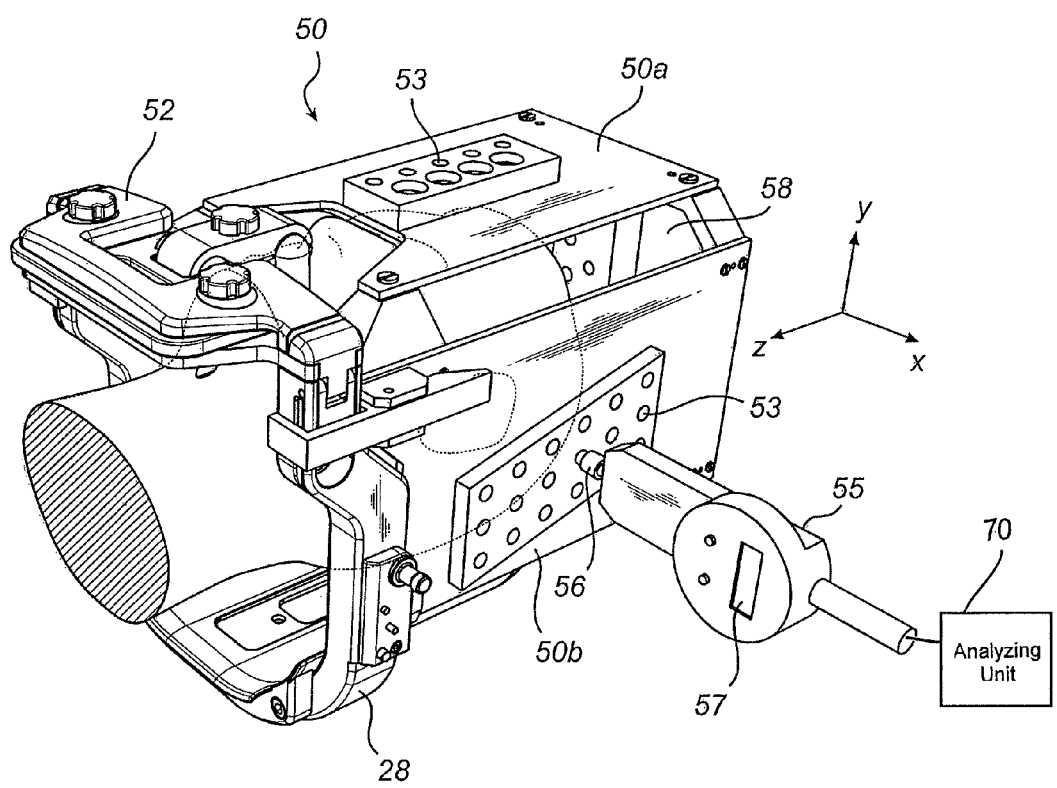
FIG. 5 illustrates another view of the head cap and measurement tool of FIG. 4.

With reference now to FIGS. 4 and 5, an embodiment of the head cap and the measurement tool according to the present invention will be discussed. In FIG. 4, an embodiment of a head cap 50 is placed onto a head 51 of a patient. The head cap 50 is mounted at a patient fixation unit or frame 52 such that the head cap 50 is flush against the frame 52, which frame is fixated to fixation arrangement 28. Thereby, it is guaranteed that patient is immobilized in relation to the radiation therapy system. The head cap 50 comprises a number of through holes 53, wherein only a few is indicated with reference numerals. The head cap 50 comprises a number of substantially plane structures, for example plane surfaces, 50a, 50b, and 50c each including a number of through holes 53. In this illustrated embodiment, the head cap 50 comprises three substantially plane surfaces 50a, 50b, and 50c including a set of through holes 53, each plane surface being substantially parallel with for an orthogonal plane in a three-dimensional coordinate system, see coordinate system in FIGS. 4 and 5. Of course, as the skilled person realizes, the head cap 50 may comprise more than three surfaces provided with through holes, for example, five or six. Furthermore, as the skilled person realizes, the surfaces may include openings 58 as shown in FIG. 4 and FIG. 5, which openings may provide improved ventilation for the patient. Further, the opening 58 also contributes to lowering the overall weight of the head cap 50. In another embodiment orthogonally arranged beams is used.

Thereby, it is possible to perform several measurements of a distance between head cap, e.g. the inner surface of the head cap, and the skull bone of the patient for three perpendicular axes and thus the accuracy and repeatability of the measurements can be increased.

Furthermore, due to the fact that the measurements can be performed plane by plane, i.e. at the planes 50a, 50b, and 50c, respectively, rotations and rotational errors can be captured, which entail that the accuracy and repeatability of the measurements can be increased.

In one embodiment of the present invention, each through hole is shaped as a substantially circular guide channel.

A measurement tool 55 is adapted to measure a distance between the head 51, or the skull bone of the head, and the head cap 53 via the through holes 53. The measurement tool comprises an elongated element 56 having an end being adapted to abut against the head 51 during a measurement to obtain at least one measurement value. In one embodiment, the elongated element 56 is spring-loaded.

The measurement tool 55 may be connected to or include an analyzing unit adapted to determine whether measurement conditions are stable. In this embodiment, as shown in FIG. 5, the analyzing unit 70 is included in the measurement tool 55. The analyzing unit may be adapted to determine a distance change over time, wherein a distance change over time being lower than a predetermined level is an indication of that the measurement conditions are stable.

In a further embodiment, the measurement tool 55 comprises a pressure indicator adapted to indicate an applied pressure of the measurement tool against the head during a measurement, wherein each measurement can be performed at a predetermined pressure. The pressure can be indicated on a display 57 of the measurement tool.

In FIG. 5, the head cap 50 and measurement tool 55 is shown in more detail.

Figure 6:
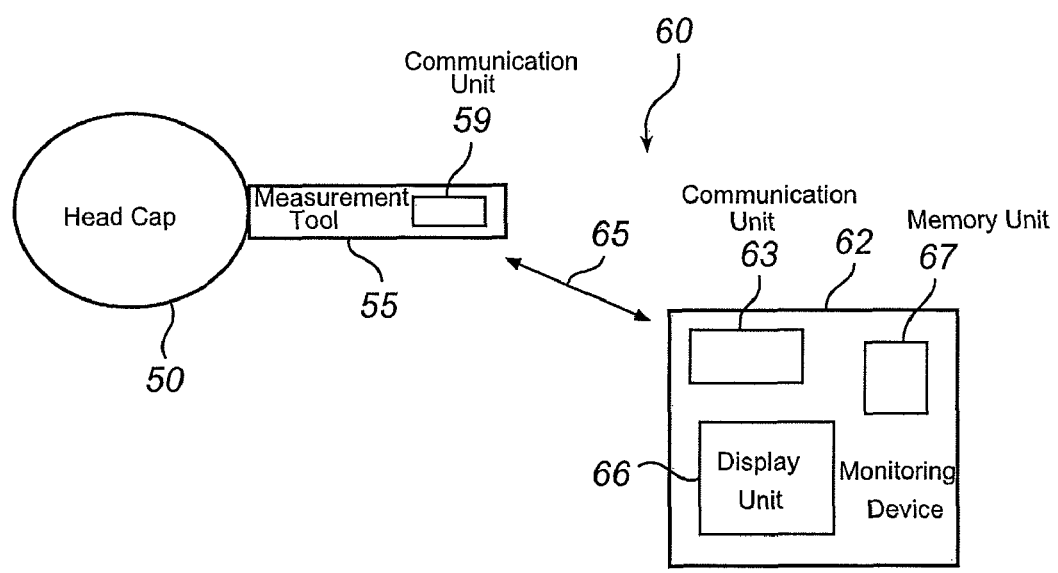
FIG. 6 illustrates measurement system according to the present invention.

In FIG. 6, a schematic view of the system according to the present invention is shown. The system 60 comprises a head cap, for example, the head cap 50 discussed above and a measurement tool 55. Furthermore, the measurement tool 55 includes a communication unit 58 adapted to communicate with an external monitoring device 62 including a communication unit 63 via a communication link 65, which may be a wireless communication link or a physical link. The communication link 65 may, for example, be a wireless LAN. The monitoring device 62 may for example be a personal computer or a lap top computer. Measurement data from the measurement tool 55 can thus be exported to the monitoring device 62 where is can be displayed on a display unit 66 and/or stored a memory unit 67.

In one embodiment of the measurement tool according to the present invention at least one predetermined conditions is that a time delay having a predetermined length has elapsed.

In another embodiment of the measurement tool according to the present invention the at least one predetermined conditions is that measurement conditions are found to be stable.

In a further embodiment of the measurement tool according to the present invention the analyzing unit is adapted to determine a distance change over time, wherein a distance change over time being lower than a predetermined level is an indication of that the measurement conditions are stable.

In yet another embodiment of the measurement tool according to the present invention a pressure indicator adapted to indicate an applied pressure of the measurement tool against said head during a measurement is included, wherein said measurement conditions are found to be stable when a predetermined pressure is indicated.

In one embodiment of the measurement tool according to the present invention the measurement tool is adapted to communicate with a monitoring device.

In an embodiment of the method according to the present invention a step of determining a position of said head of said patient relatively to a reference position by comparing said obtained measurement values with corresponding reference values is included.

In another embodiment of the method according to the present invention the step of performing a measurement session comprises the steps of:

guiding an elongated element of said measurement tool comprising a rod through a first through hole and placing said elongated element such that an end of said elongated element abuts against said head;

obtaining at least one measurement value including a distance between the head of said patient and a respective reference point of said head cap using the measurement tool;

removing said measurement tool when said at least one measurement value has been obtained; and repeating said step of passing and removing for a number of selected through holes during the measurement session.

In a further embodiment of the method according to the present invention the step of performing a measurement session comprises the steps of:

after said end of said elongated element has been placed to abut against said head, determining whether at least one predetermined condition is satisfied; and when it has been determined that said at least one predetermined conditions is satisfied, obtaining at least one measurement value between the head of said patient and a respective reference point of said head cap using the measurement tool.

In another embodiment of the method according to the present invention the at least one predetermined condition is a time delay having a predetermined length has elapsed.

In yet another embodiment of the method according to the present invention the at least one predetermined conditions is that measurement conditions are found to be stable.

In a further embodiment of the method according to the present invention the step of determining whether said at least one predetermined conditions is satisfied comprises the steps of:

determine a distance change over time, wherein a distance change over time being lower than a predetermined level is an indication of that the measurement conditions are stable; and when it has been determined that the measurement conditions are stable, obtaining at least one measurement value between the head of said patient and a respective reference point of said head cap using the measurement tool.

In another embodiment of the method according to the present invention the measurement conditions are found to be stable when a predetermined pressure is indicated.

In one embodiment of the method according to the present invention the step of performing a measurement session comprises the step of obtaining a predetermined number of measurement values at each axis of a three dimensional orthogonal reference coordinate system of the frame.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A system for measuring a position of a head of a patient during neurological diagnosis, therapy or surgery, relative to a frame adapted to be fixated to a diagnosis equipment, said frame being fixated relative to said patient, said system comprising a head cap adapted to be mounted at said frame such that said head cap is fixed relative to said frame, said head cap being rigid and shaped such that the head of said patient is at least partly surrounded when said head cap is placed on said head, wherein said head cap includes a number of through holes; and a measurement tool comprising an elongated element, said measurement tool being adapted to measure a distance between said head and said head cap via a through hole through said elongated element, said elongated element is spring-loaded and has an end adapted to abut against said head during a measurement, wherein said measurement tool is adapted to obtain at least one measurement value indicating a position of said head in relation to said head cap substantially without operator interaction.

2. The system according to claim 1, wherein said measurement tool comprises a distance meter adapted to deliver a distance measure indicating a distance between said head and a reference point of said head cap, wherein each through hole has a reference point.

3. The system according to claim 2, wherein said head cap comprises a number of plane structures each including at least one through hole.

4. The system according to claim 2, wherein said measurement tool comprises an analyzing unit adapted to determine whether at least one predetermined condition is satisfied and wherein said measurement tool is adapted to obtain said at least one measurement value indicating a position of said head in relation to said head cap when said at least one predetermined condition is satisfied.

5. The system according to claim 1, wherein said head cap comprises a number of plane structures each including at least one through hole.

6. The system according to claim 1, wherein said measurement tool comprises an analyzing unit adapted to determine whether at least one predetermined condition is satisfied and wherein said measurement tool is adapted to obtain said at least one measurement value indicating a position of said head in relation to said head cap when said at least one predetermined condition is satisfied.

7. The system according to claim 6, wherein said at least one predetermined condition is that a time delay having a predetermined length has elapsed.

8. The system according to claim 6, wherein said analyzing unit is adapted to determine a distance change over time, and wherein said at least one predetermined condition is that said distance change over time is lower than a predetermined level.

9. The system according to claim 1, wherein said measurement tool comprises a pressure indicator adapted to indicate an applied pressure of said measurement tool against said head during a measurement, wherein said measurement tool is adapted to obtain said at least one measurement value indicating a position of said head in relation to said head cap when a predetermined pressure is indicated.

10. The system according to claim 1, wherein said head cap comprises a first plane structure including at least one through hole arranged such that an imaginary line passing through said hole is substantially parallel with a first axis of a three dimensional orthogonal reference coordinate system of the frame, wherein said head cap comprises a second plane structure including at least one through hole arranged such that an imaginary line passing through said hole is substantially parallel with a second axis of said reference coordinate system, and wherein said head cap comprises a third plane structure including at least one through hole arranged such that an imaginary line passing through said hole is substantially parallel with a third axis of said reference coordinate system.

11. The system according to claim 1, further comprising a monitoring device adapted to receive said at least one measurement value from said measurement tool, wherein said measurement tool is adapted to communicate with said monitoring device.

12. A measurement tool for use in a system for measuring a position of a head of a patient during neurological diagnosis, therapy or surgery, relative to a frame adapted to be fixated to a diagnosis equipment, said frame being fixated relative to said patient, said system further comprising a head cap adapted to be mounted at said frame such that said head cap is fixed relatively said frame, said head cap being rigid and shaped such that the head of said patient is at least partly surrounded when said head cap is placed on said head, and wherein said head cap comprises a number of plane structures each including at least one through hole, said measurement tool comprising an elongated element, said elongated element being spring-loaded and including an end configured to abut against said head during a measurement, wherein said measurement tool is adapted to measure a distance between said head and said head cap via a through hole through said elongated element, wherein said measurement tool is adapted to obtain at least one measurement value indicating a position of said head in relation to said head cap without operator interaction.

13. The measurement tool according to claim 12, wherein said measurement tool comprises an analyzing unit adapted to determine whether at least one predetermined condition is satisfied and wherein said measurement tool is adapted to obtain said at least one measurement value indicating a position of said head in relation to said head cap when said at least one predetermined condition is satisfied.

14. A method for measuring a position of a head of a patient during neurological diagnosis, therapy or surgery, relative to a frame adapted to be fixated to a radiation therapy unit, said frame being fixated relative to said patient, said method comprising a. providing a head cap adapted to be mounted at said frame such that said head cap is fixed relatively said frame, said head cap being rigid and shaped such that the head of said patient is at least partly surrounded when said head cap is placed on said head, wherein said head cap comprises a number of through holes;

b. placing said head cap on the head of tile patient;

c. fixating said head cap to said frame:

d. providing a measurement tool adapted to measure a distance between said head and said head cap via a through hole by an elongated element being spring-loaded and having an end being adapted to abut against said head during a measurement, wherein said measurement tool is adapted to obtain at least one measurement value indicating a position of said head in relation to said head cap without operator interaction; and e. performing a measurement session in order to obtain a plurality of measurement values each including a distance between the head of said patient and a respective reference point of said head cap using the measurement tool.

* * * * *